United States Patent [19]
O'Lenick, Jr. et al.

[11] Patent Number: 6,069,273
[45] Date of Patent: May 30, 2000

[54] ALKOXYLATED FLUORO ESTERS CARBOXYLATES

[75] Inventors: Anthony J. O'Lenick, Jr.; Jeff K. Parkinson, both of Dacula; Robert T. Torbush, Snellville, all of Ga.

[73] Assignee: Lambert Technologies Inc, Norcross, Ga.

[21] Appl. No.: 09/223,100

[22] Filed: Dec. 30, 1998

Related U.S. Application Data

[62] Division of application No. 09/017,333, Feb. 2, 1998, Pat. No. 5,969,177.

[51] Int. Cl.$^7$ .................................................. C07C 59/00
[52] U.S. Cl. ............................................................. 562/586
[58] Field of Search ............................................. 562/586

[56] References Cited

U.S. PATENT DOCUMENTS 5,296,625  3/1994  O'Lenick, Jr. et al. ................ 556/437

*Primary Examiner*—Gary Geist
*Assistant Examiner*—Taylor V. Oh

[57] ABSTRACT

The invention relates to a series of novel alkoxylated fluoro esters which contain a terminal carboxy group. This class of compounds provides unique solubility in many organic solvents as well as very substantive salts of the carboxylic acid when neutralized with base. In addition, the compounds of the present invention have tremendous spreadability when applied to substrate. The compounds of the present invention are prepared by reacting a the hydroxyl group in a fluoro alcohol with an anhydride.

8 Claims, No Drawings

ALKOXYLATED FLUORO ESTERS CARBOXYLATES

RELATED APPLICATIONS

This application is a divisional application of Ser. No. 09/017,333 filed Feb. 2, 1998, now U.S. Pat. No. 5,969,177.

BACKGROUND OF THE INVENTION

1. Field of the Invention

The present invention relates to a series of novel fluoro alkoxylated esters which have a terminal carboxy group. These materials provide outstanding lubrication, and softening when applied to a variety of fiber substrates. The compounds of the present invention are prepared by reacting a fluoro alcohol and an anhydride.

2. Arts and Practices

U.S. Pat. No. 5,296,625 to O'Lenick et al, incorporated herein by reference, discloses silicone carboxylate esters. The compounds of the O'Lenick et al invention are softeners and conditioners, but as will become clear are not good spreading agents. The ability to provide thin films to plastic and other substrates was lacking in the O'Lenick et al products.

The compounds of the present invention address deposition on fabric and skin of a highly lubricious, cost-effective lubricant. In addition, the compounds of the present invention have tremendous spreadability when applied to substrate. This spreadability results in thin, highly lubricating films. The thinness of the film makes the delivery of an expensive fluoro compound cost-effective on many substrates, since the weight of film per area of substrate treated is quite surprisingly low. The compounds of the present invention find use not only in applications on substrate like plastics and textile fibers and fabric, but can be used in personal care products, like shave cream and hair conditioners, where the lubrication afforded by using the compounds of the current invention provide a close, more comfortable shave and outstanding wet comb properties on hair.

THE INVENTION

OBJECT OF THE INVENTION

It is the object of the present invention to provide novel alkoxylated fluoro ester having a carboxy group present.

tremendous spreadability when applied to substrate. This spreadability results in thin highly lubricating films. The thinness of the film makes the delivery of an expensive fluoro compound cost effective on many substrates, since the weight of film per area of substrate treated is quite surprisingly low.

It is another objective of the current invention to provide fluoro ester carboxylates which can be used in personal care, textile, and industrial formulations to render softness and lubrication to the substrates being treated. The superior solubility properties are an important benefit, since this is a major aspect of consumer perception of softness in consumer and industrial laundry applications. Application of the compounds of the invention can be from solvent, aqueous dispersion or solution, or applied neat in these processes.

SUMMARY OF THE INVENTION

The present invention relates to novel fluoro alkoxylated esters which contain carboxyl groups. The compounds by virtue of the polyoxyalkylene group are soluble in a variety of organic and aqueous systems, but have many of the functional softening and lubrication properties of fluoro carbons. The solubility of these materials can be altered by simple pH adjustment. In the acid form these materials are fluoro-like it their solubility parameters. At higher pH values they become soluble in aqueous systems. This property makes these materials excellent additives for highly effective surface modifying finishes for fiber and textiles. The compounds of the present invention are substantive to cellulosic and synthetic fibers as well as metal surfaces and plastic polymers.

As will become clear from the disclosure, the compounds of the present invention while having fluorine groups present in the molecule, have unique solubility aqueous systems. This property is a direct result of the structure. The pendant group needs to contain (a) a fluoro group linked covalently through two methylene groups to (b) an alkoxylated portion linked covalently to (c) an ester function, linked covalently to (d) an R" linking group containing carbon atoms linked covalently to (E) a COOH group. Compounds lacking these functional parts do not give the desired solubilization properties. Optionally the carboxyl group can be neutralized with a base or an amine to give an ionic compound.

The compounds of the present invention therefore have a pendant group which is as follows:

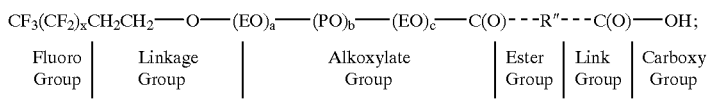

| Fluoro Group | Linkage Group | Alkoxylate Group | Ester Group | Link Group | Carboxy Group |

These compounds are outstanding lubricants that are substantive to the surface of a fiber and other textile materials including cellulosic material and have increased solubility in fatty materials including mineral oil, fatty triglycerides and traditional fatty quaternary ammonium compounds. The compounds of the present invention render the lubricity and by controlling the amount and placement of alkylene oxide in the molecule, can have significantly different solubilities in water. In one embodiment, the compounds have a high cloud point due to the presence of a polyoxyethylene group. This allows for deposition on fabric and skin upon heating. In addition, the compounds of the present invention have wherein;

EO is —(CH$_2$CH$_2$O)—

PO is —(CH$_2$—CH(CH$_3$)CH$_2$—O)—

The fluoro Group is soluble in fluoro carbon based materials; the alkoxylate group renders water solubility to the molecule; the ester linkage taken with the carbon linkage group made up the oil soluble group and the terminal group is the ionizable group.

These materials will allow for the solubilization of water, and fluoro carbons into one phase. Standard surface active agents or surfactants have only water soluble portion and an oil soluble portion. A standard fatty surfactant has only a fatty and a water soluble:

$$CH_3-(CH_2)_{17}-O-(CH_2CH_2-O)_{10}-H$$

Fatty Portion | Water Soluble Portion

This type of material will allow for solubilization of fatty oils and water, but not fluoro carbons.

Fluoro carbons, on the other hand have a fluoro portion and a water soluble portion. These materials allow for the solubilization of fluoro carbons, but not water.

There are many instances where there is a desire to make water and fluoro carbon stay in a single system. Each component is insoluble in each other. The compounds of the present invention not only allow for preparation of water in fluoro hydrocarbon emulsions, but also fluorocarbon in water emulsions.

The compounds of the present invention are prepared by the reaction of an anhydride with a fluoro alkoxy alcohol. Suitable anhydrides for the preparation of the compounds of the present invention are cyclic anhydrides, which react easily at mild conditions with the hydroxyl group to produce an ester carboxylate. Typical of the reaction is the following sequence utilizing succinic anhydride:

Fluoro-OH + [succinic anhydride] ----> Fluoro-O—C(O)—CH$_2$—CH$_2$—C(O)OH

The Fluoro—OH represents the hydroxyl group on the fluoro hydrocarbon described elsewhere in the disclosure.

The compounds of this invention are fluoro ester carboxylates made by the reaction of an anhydride and a hydroxy containing fluoro compound. The compounds of the present invention conform to the following structure:

$$CF_3(CF_2)_xCH_2CH_2-O-R-C(O)-R''-C(O)-OH$$

wherein;

R is —(CH$_2$CH$_2$—O)$_a$—(CH$_2$CH(CH$_3$)O)$_b$—(CH$_2$CH$_2$O)$_c$—

R'' is selected from —CH$_2$—CH$_2$—; —CH=CH;

—CH$_2$—C(R$^1$)—H;

[benzene ring structure] and [chlorinated benzene ring structure];

R$_1$ is alkyl having from 1 to 20 carbon atoms;
a, b and c are integers independently ranging from 0 to 20,
x is an integer ranging from 1 to 10.

PREFERRED EMBODIMENTS

In a preferred embodiment, a+b+c is greater than zero.
In another preferred embodiment, the R'' is —CH$_2$—CH$_2$—.
In still another embodiment R'' is —CH=CH—.
In another preferred embodiment R'' is —CH$_2$—C(R$^1$)—H.

In still another preferred embodiment R'' is

[benzene ring structure]

In still another preferred embodiment R'' is

[chlorinated benzene ring structure]

In still another preferred embodiment R$^1$ is alkyl having from 6 to 20 carbon atoms.

In a more preferred embodiment R$^1$ is alkyl having from 12 to 20 carbon atoms.

EXAMPLES

The compounds of the present invention are prepared by the reaction of a hydroxy fluoro compound and an anhydride. Examples of suitable reactants are as follows:

REACTANTS

Anhydrides

The various anhydrides listed are all items of commerce and are prepared by methods known to those skilled in the art.

Reactant Example I (Succinic Anhydride)

[succinic anhydride structure]

Reactant Example II (Alkyl Succinic Anhydride)

[alkyl succinic anhydride structure]

Reactant Example III (Alkyl Succinic Anhydride)

$$\text{C}_{12}\text{H}_{25}-\underset{\underset{\text{H}}{|}}{\text{C}}\underset{\diagdown}{\overset{\text{O}=\text{C}\diagup^{\text{O}}\diagdown\text{C}=\text{O}}{|}}\text{CH}_2$$

Reactant Example IV (Alkyl Succinic Anhydride)

$$\text{C}_{6}\text{H}_{13}-\underset{\underset{\text{H}}{|}}{\text{C}}\underset{\diagdown}{\overset{\text{O}=\text{C}\diagup^{\text{O}}\diagdown\text{C}=\text{O}}{|}}\text{CH}_2$$

Reactant Example V (Alkyl Succinic Anhydride)

$$\text{C}_{18}\text{H}_{37}-\underset{\underset{\text{H}}{|}}{\text{C}}\underset{\diagdown}{\overset{\text{O}=\text{C}\diagup^{\text{O}}\diagdown\text{C}=\text{O}}{|}}\text{CH}_2$$

Reactant Example VI (Alkyl Succinic Anhydride)

$$\text{C}_{20}\text{H}_{41}-\underset{\underset{\text{H}}{|}}{\text{C}}\underset{\diagdown}{\overset{\text{O}=\text{C}\diagup^{\text{O}}\diagdown\text{C}=\text{O}}{|}}\text{CH}_2$$

Reactant Example VII (Maleic Anhydride)

$$\text{O}=\text{C}\diagup^{\text{O}}\diagdown\text{C}=\text{O}\atop{\text{HC}-\text{CH}}$$

Reactant Example VIII (Phthalic Anhydride)

[Structure of phthalic anhydride]

Reactant Example IX (Tetrachlorophthalic anhydride)

[Structure of tetrachlorophthalic anhydride]

Hydroxy Fluoro Compounds

Many manufacturers offer a series of hydroxy fluoro compounds suitable for use as raw materials in the preparation of the esters of the present invention. These materials are marketed under the many trade names. Dupont manufacturers and offers the compounds commercially.

A key structural attribute of the compounds of the present invention is the two methylene groups between the fluoro part of the molecule and the oxygen. The structure of the stable alcohol is $CF_3(CF_2)_x CH_2 CH_2$—OH. If the two methylene groups (—$CH_2$—) are absent the alcohol is not stable to hydrolysis.

| Example | x  | a  | b  | c  |
|---------|----|----|----|----|
| 1       | 1  | 20 | 20 | 20 |
| 2       | 2  | 10 | 5  | 10 |
| 3       | 4  | 0  | 10 | 0  |
| 4       | 6  | 5  | 5  | 5  |
| 5       | 8  | 0  | 0  | 0  |
| 6       | 10 | 5  | 1  | 5  |
| 7       | 8  | 10 | 0  | 0  |
| 8       | 10 | 5  | 0  | 0  |

General Reaction Conditions

The reaction can be run with either a stiochiometric amount of the anhydride, or an excess of fluoro polymer.

Into a suitable round bottom, three neck flask equipped with a thermometer and a nitrogen sparge is added the specified number of grams of the specified fluoro compound and the specified number of grams of the specified anhydride. The reaction mass is blanketed with nitrogen, and heated to 80 and 110 C. under the inert nitrogen blanket. Within four to five hours the theoretical acid value is obtained. The product is a clear liquid and is used without additional purification.

Example 9

Into a suitable round bottom, three neck flask equipped with a thermometer and a nitrogen sparge is added 2468.0 grams of fluoro example 2 and the 100.0 grams of succinic anhydride. The reaction mass is then blanketed with nitrogen and heated to 80 and 110 C. This temperature is maintained for four to five hours. The theoretical acid value is obtained. The product is a clear liquid and is used without additional purification.

Examples 10–17

Example 9 is repeated only this time substituting the specified number of grams of the anhydride specified and the specified type and number of grams of fluoro compound as shown below;

| | Anhydride | | Fluoro Compound | |
|---|---|---|---|---|
| | Reactant | | | |
| Example | Example | Grams | Example | Grams |
| 9 | I | 100.0 | 1 | 3303.0 |
| 10 | II | 115.0 | 2 | 2468.0 |
| 11 | III | 269.0 | 3 | 1103.0 |
| 12 | IV | 185.0 | 4 | 1348.0 |
| 13 | V | 316.0 | 5 | 713.0 |
| 14 | VI | 340.0 | 6 | 1253.0 |
| 15 | VII | 98.0 | 7 | 1153.0 |
| 16 | VIII | 148.0 | 6 | 1253.0 |
| 17 | IX | 288.0 | 8 | 1033.0 |

Applications

The compounds of the present invention have tremendous spreadability when applied to substrate. This spreadability results in thin highly lubricating films. The thinness of the film makes the delivery of an expensive fluoro compound cost effective on many substrates, since the weight of film per area of substrate treated is quite surprisingly low.

Spreadability Test 10 microliters of sample was applied to a polyethylene film and the area covered by the spreading of the material was evaluated. The value obtained was compared to water and nonylphenol that has been ethoxylated with nine moles of ethylene oxide.

Spreadability

| Sample Tested | Spread Area (Cm$^2$) |
|---|---|
| Example 15 | 502.0 |
| Example 17 | 486.0 |
| Ethoxylated Nonyl phenol (9 moles) | 99.3 |
| Carboxy Silicone (U.S. Pat. 5,296,625) Example 22 | 127.7 |
| Water | 64.6 |

Relative Spreadability

| Sample Tested | Spread Area (Cm$^2$) |
|---|---|
| Example 15 | 7.8 |
| Example 17 | 7.5 |
| Ethoxylated Nonyl phenol (9 moles) | 1.5 |
| Carboxy Silicone (U.S. Pat. 5,296,625) Example 22 | 2.0 |
| Water | 1.0 |

As can be seen by the above data, the fluoro alkoxylated ester of the current invention is by far the best spreading agent of those tested. NP-9 is a standard fatty surfactant, and the carboxy silicone of the O'Lenick invention is the closest silicone analogue of the current invention. All materials clearly spread less well than the products of the current invention.

What is claimed:

1. A fluoro ester conforming to the following structure;

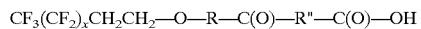

$$CF_3(CF_2)_xCH_2CH_2-O-R-C(O)-R''-C(O)-OH$$

wherein;

R is $-(CH_2CH_2-O)_a-(CH_2CH(CH_3)O)_b-(CH_2CH_2O)_c-$;

R" is $-CH_2-CH_2$;

a, b and c are integers independently ranging from 0 to 20, with the proviso that a+b+c is greater than 0;

x is an integer ranging from 1 to 10.

2. A fluoro ester of claim 1 wherein x is 1, a is 20, b is 20 and c is 20.

3. A fluoro ester of claim 1 wherein x is 2, a is 10, b is 5 and c is 10.

4. A fluoro ester of claim 1 wherein x is 4, a is 0, b is 10 and c is 0.

5. A fluoro ester of claim 1 wherein x is 6, a is 5, b is 5, and c is 5.

6. A fluoro ester of claim 1 wherein x is 10, a is 5, b is 1 and c is 5.

7. A fluoro ester of claim 1 wherein x is 8, a is 10, b is 0 and c is 0.

8. A fluoro ester of claim 1 wherein x is 10, a is 5, b is 0 and c is 0.

* * * * *